(12) United States Patent
Ito et al.

(10) Patent No.: US 6,639,089 B2
(45) Date of Patent: Oct. 28, 2003

(54) ANTICANCER AGENTS, PERFUMES OR FOODS AND DRINKS

(75) Inventors: Nobuhiko Ito, Noda (JP); Hiroyuki Tsuji, Tokyo (JP); Yoshio Fukuda, Tokyo (JP)

(73) Assignee: Soda Aromatic Co., Ltd.

( * ) Notice: Subject to any disclaimer, the term of this patent is extended or adjusted under 35 U.S.C. 154(b) by 0 days.

(21) Appl. No.: 10/169,527

(22) PCT Filed: Nov. 1, 2001

(86) PCT No.: PCT/JP01/09661

§ 371 (c)(1),
(2), (4) Date: Jul. 2, 2002

(87) PCT Pub. No.: WO02/38148

PCT Pub. Date: May 16, 2002

(65) Prior Publication Data

US 2003/0055105 A1 Mar. 20, 2003

(30) Foreign Application Priority Data

Nov. 5, 2001 (JP) .......................... 2000-340459

(51) Int. Cl.[7] ............................................. C07C 59/245
(52) U.S. Cl. .................... 554/115; 554/213; 514/400; 514/557; 514/675; 514/680; 514/685
(58) Field of Search ................. 514/675, 680, 514/685, 450, 557; 554/213, 115

(56) References Cited

U.S. PATENT DOCUMENTS 6,057,372 A  *  5/2000  Nobuhiro et al. ........... 514/675

FOREIGN PATENT DOCUMENTS

| EP | 503312 | * | 2/1992 |
| JP | 01/172359 | * | 7/1989 |
| JP | 163744 | * | 6/2001 |
| WO | 97/47294 | * | 12/1997 |

OTHER PUBLICATIONS

Nobuhiro et al., Antibacterial Property or Macrocyclic Aromatic Compounds (Part 2) —Antibacterial Property against Oral Bacteria, 43rd Symposium on the Chmaistry of Terpenes, Essentical Oils, and Aromatics, pp. 135–137, Sep. 1999.*

* cited by examiner

Primary Examiner—Deborah D. Carr
(74) Attorney, Agent, or Firm—Piper Rudnick LLP

(57) ABSTRACT

Anticancer agents containing, as an active ingredient, at least one compound selected from the group consisting of ω-hydroxy fatty acids and salts or esters thereof, hydroxy oxo-fatty acids and salts or esters thereof, lactones, macrocyclic ketones, and macrocyclic diesters having specific chemical structures.

23 Claims, No Drawings

ANTICANCER AGENTS, PERFUMES OR FOODS AND DRINKS

TECHNICAL FIELD

The present invention relates to drugs and, particularly, to anticancer agents. More particularly, the present invention relates to an anticancer agents containing, as an active ingredient, at least one compound selected from the group consisting of ω-hydroxy fatty acids and salts or esters thereof, hydroxy oxo-fatty acids and salts or esters thereof, lactones, macrocyclic ketones, and macrocyclic diesters.

BACKGROUND ART

Many anticancer agents, including bleomycin, Pepleostatin, and Mitomycin (registered trade name), have been developed. However, these agents have strong side effects, such as cytotoxicity, and moreover, in order to exert a satisfactory action of inhibiting metastasis, they must be administered in large quantities, which may prove to be fatal.

Under the circumstances, attention has been given to the development of compounds having decreased side effects. As a result, antitumor agents containing carbon, hydrogen, and oxygen only have been proposed, for example, antitumor agents containing unsaturated fatty acids, such as linoleic acid and oleic acid (disclosed in JP-A-Syouwa62-12716, etc.), ketol-type unsaturated fatty acids (disclosed in JP-A-Heisei5-279252), hydroxylinoleic acid (disclosed in JP-A-Heisei7-291862), and 10-oxo-11(E)-octadecen-13-olide, which is a new macrolide compound (disclosed in JP-A-Heisei6-220037).

However, in these antitumor agents, merely the action of killing tumors is demonstrated, and since known antitumor agents use natural extracts as raw materials, in order to ensure purities necessary for antitumor agents, extremely complex purifying processes must be performed, resulting in production difficulty on an industrial scale.

Accordingly, it is an object of the present invention to provide an anticancer agents which is easily produced, which has an activity of inhibiting cancer metastasis in addition to an activity of killing cancer, and which also has decreased side effects.

DISCLOSURE OF THE INVENTION

"Anticancer agents" in the present invention mean agents which are used for the purpose of killing cancer, inhibiting the metastasis of cancer, preventing the recurrence of cancer, preventing cancer, or the like.

The present inventors have carried out thorough research on substances which can be mass-produced in high purities on an industrial scale, which are highly safe, and which exhibit satisfactory absorption into cells, and found that ω-hydroxy fatty acids and salts or esters thereof, hydroxy oxo-fatty acids and salts or esters thereof, lactones, macrocyclic ketones, and macrocyclic diesters having specific chemical structures are anticancer agents which have significantly high activities of killing cancer and inhibiting the metastasis of cancer, and thus the present invention has been achieved.

In one aspect of the present invention, the anticancer agents contain, as an active ingredient, at least one compound selected from the group consisting of:

an ω-hydroxy fatty acid represented by general formula (1) or a salt or ester thereof:

$$HO-R_1-COOH \qquad (1)$$

wherein $R_1$ is a straight carbon chain having 10 to 25 carbon atoms, with no or one double bond, where an alkyl or alkylene group having 1 to 4 carbon atoms or a hydroxyl group may be linked to any position as a side chain;

a hydroxy oxo-fatty acid represented by general formula (2) or a salt or ester thereof:

$$R_2-COOH \qquad (2)$$

wherein $R_2$ is a saturated straight carbon chain having 9 to 25 carbon atoms, with at least one carbonyl group and at least one hydroxyl group, where an alkyl or alkylene group having 1 to 4 carbon atoms may be linked to any position as a side chain;

a lactone represented by general formula (3):

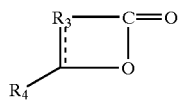

(3)

wherein $R_3$ is a carbon chain having 2 to 24 carbon atoms which is saturated or unsaturated by including at least one carbon-carbon double bond in any position, or a carbon chain having 8 to 24 carbon atoms with at least one oxygen atom in any position which is saturated or unsaturated by including at least one carbon-carbon double bond in any position, where an alkyl or alkylene group having 1 to 4 carbon atoms may be linked to any position as a side chain; $R_4$ is hydrogen, a hydroxyl group, or a carbon chain having 1 to 30 carbon atoms which is saturated or unsaturated by including at least one carbon-carbon double bond in any position, where an alkyl or alkylene group having 1 to 4 carbon atoms may be linked to any position; and the dashed line represents a single bond or a double bond;

a macrocyclic ketone represented by general formula (4):

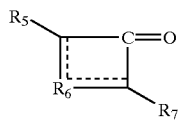

(4)

wherein $R_5$ is hydrogen or an alkyl or alkylene group having 1 to 4 carbon atoms; $R_6$ is a carbon chain having 7 to 17 carbon atoms which is saturated or unsaturated by including at least one carbon-carbon double bond in any position, where an alkyl or alkylene group having 1 to 4 carbon atoms may be linked to any position as a side chain; $R_7$ is hydrogen or an alkyl group or an alkylene group having 1 to 4 carbon atoms; and the dashed line represents a single bond or a double bond; and a macrocyclic diester represented by general formula (5)

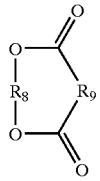

(5)

wherein $R_8$ is a carbon chain having 2 to 10 carbon atoms which is saturated or unsaturated by including at least one carbon-carbon double bond in any position, where an alkyl or alkylene group having 1 to 4 carbon atoms may be linked to any position; and $R_9$ is a carbon chain having 8 to 20 carbon atoms which is saturated or unsaturated by including at least one carbon-carbon double bond in any position.

That is, as described above, the anticancer agents of the present invention contains, as an active ingredient, at least one compound selected from the group consisting of ω-hydroxy fatty acids and salts or esters thereof, hydroxy oxo-fatty acids and salts or esters thereof, lactones, macrocyclic ketones, and macrocyclic diesters. These compounds used in the present invention can be combined with the existing anticancer agents.

In the meantime, although various methods for making ω-hydroxy fatty acids are known, since many types of impurities are produced due to various side reactions in all of the methods, in order to highly purify the resultant ω-hydroxy fatty acids, complex purification processes must be performed. However, as a result of thorough research carried out by the present inventors, it has been found that by opening the ring of the lactone of the present invention by hydrolysis, an ω-hydroxy fatty acid can be obtained in high purities in a significantly simple way, and thus the present invention has been achieved.

All of the ω-hydroxy fatty acids and salts or esters thereof, hydroxy oxo-fatty acids and salts or esters thereof, lactones, macrocyclic ketones, and macrocyclic diesters used in the present invention, as compounds themselves, include known compounds, and have been industrially mass-produced mainly as raw materials for perfume compounds and as perfume compounds.

That is, with respect to the compounds used in the present invention, the industrial production methods therefor have been established and they have previously been used for fragrance materials rather than anticancer agents, i.e., they are readily available compounds with high purities.

As the ω-hydroxy fatty acid or a salt or ester thereof used in the present invention, any compound represented by the following general formula (1) may be used:

HO—$R_1$—COOH                                    (1)

wherein $R_1$ is a straight carbon chain having 10 to 25 carbon atoms, with no or one double bond, where an alkyl or alkylene group having 1 to 4 carbon atoms or a hydroxyl group may be linked to any position as a side chain. Preferably, $R_1$ is a straight carbon chain which is saturated or which has one double bond, in which a hydroxyl group is linked to the ω position. Preferred examples of ω-hydroxy fatty acids include 12-hydroxydodecanoic acid, 14-hydroxytetradodecanoic acid, 15-hydroxypentadecanoic acid, 16-hydroxyhexadecanoic acid, 17-hydroxyheptadecanoic acid, 18-hydroxyoctadecanoic acid, 15-hydroxy-11-pentadecenoic acid, 15-hydroxy-12-pentadecenoic acid, 16-hydroxy-9-hexadecenoic acid, and 16-hydroxy-7-hexadecenoic acid. Preferred examples of esters include ethyl esters and n-propyl esters of these ω-hydroxy fatty acids.

These ω-hydroxy fatty acids may be produced by any known method. More preferably, in order to easily obtain high-purity products, the ring of a lactone represented by the following general formula (3) is opened, for example, by alkaline hydrolysis, and then acid treatment is performed:

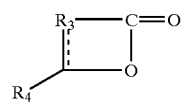

(3)

wherein $R_3$ is a carbon chain having 8 to 24 carbon atoms which is saturated or unsaturated by including one or two carbon-carbon double bonds in any positions, where an alkyl or alkylene group having 1 to 4 carbon atoms may be linked to any position as a side chain; $R_4$ is hydrogen or an alkyl or alkylene group having 1 to 4 carbon atoms; and the dashed line represents a single bond or a double bond. Additionally, with respect to the lactones used as the raw materials, the industrial production methods have been established, and they have already been mass-produced as fragrance materials. Therefore, high-purity products can be more easily obtained by using them.

As the hydroxy oxo-fatty acid or a salt or ester thereof used in the present invention, any compound represented by the following general formula (2) may be used:

$R_2$—COOH                                      (2)

wherein $R_2$ is a saturated straight carbon chain having 9 to 25 carbon atoms, with at least one carbonyl group and at least one hydroxyl group, where an alkyl or alkylene group having 1 to 4 carbon atoms may be linked to any position as a side chain. Preferably, the hydroxyl group is located at the ω position of $R_2$ in the formula because the industrial production method therefor has been established. Preferably, the number of carbonyl groups is one, and the carbonyl group is located at the (ω-3) position. More preferred is any one of 11-hydroxy-8-oxoundecanoic acid, 12-hydroxy-9-oxododecanoic acid, 13-hydroxy-10-oxotridecanoic acid, 14-hydroxy-11-oxotetradecanoic acid, 15-hydroxy-12-oxopentadecanoic acid, 16-hydroxy-13-oxohexadecanoic acid, 17-hydroxy-14-oxoheptadecanoic acid, 18-hydroxy-15-oxooctadecanoic acid, 19-hydroxy-16-oxononadecanoic acid, 20-hydroxy-17-oxoeicosanoic acid, and 21-hydroxy-18-oxoheneicosanoic acid. More preferred examples of esters include ethyl esters and n-propyl esters of these hydroxy oxo-fatty acids.

As the method for producing the hydroxy oxo-fatty acids, any appropriate known method may be used. For example, International Patent Application Publication No. WO97/06156 discloses that an ω-hydroxy-(ω-3)-keto-fatty acid is produced by condensing γ-butyrolactone with an ester of dicarboxylic acid, followed by hydrolysis and decarboxylation. Japanese Patent No. 2595094 also discloses a method in which an α-(ω-cyanoalkanoyl)-γ-butyrolactone is used as a raw material, and hydrolysis and decarboxylation are performed to produce an ω-hydroxy-(ω-3)-keto-fatty acid.

The ω-hydroxy fatty acids represented by the general formula (1) described above, the salts or a salt thereof can be easily obtained as high-purity products either by hydrolyzing lactones using acids or alkalis, followed by recrystallization, or by further performing acidification after hydrolysis in the case of alkaline hydrolysis, followed by recrystallization or purification by distillation.

In the present invention, although the acid used for hydrolysis of the lactone described above is not particularly limited as long as the lactone can be hydrolyzed, at least one mineral acid, such as hydrochloric acid, sulfuric acid, phosphoric acid, or nitric acid is preferably used.

Although the alkali used for hydrolysis of the lactone described above is not particularly limited as long as the lactone can be hydrolyzed, lithium hydroxide, sodium hydroxide, potassium hydroxide, cesium hydroxide, lithium carbonate, sodium carbonate, potassium carbonate, cesium carbonate, or the like is preferably used, and two or more of these may be used in combination.

In the hydrolysis in the present invention, the equivalent weight of the acid or alkali used is desirably 0.7 or more relative to the lactone, preferably 1 to 10, and more preferably 1 to 3. The solvent used in the hydrolysis is not particularly limited as long as it is a mixed solvent with water or a water-soluble solvent. Examples of water-soluble solvents include methanol, ethanol, propanol, 2-propanol, acetone, tetrahydrofuran, ethylene glycol, ethylene glycol monomethyl ether, ethylene glycol dimethyl ether, and 1,4-dioxane, and a mixed solvent including at least one of these in a certain ratio may be used.

When alkali hydrolysis is performed, by recrystallizing the solution of the alkali salt obtained under the conditions described above, an ω-hydroxy fatty acid salt can be obtained in high purities. Furthermore, by subjecting the ω-hydroxy fatty acid salt to acid treatment after the hydrolysis, an ω-hydroxy fatty acid may be obtained. Although the acid used in the acid treatment is not particularly limited as long as it neutralizes and then acidifies the alkali salt in which the ring has been opened by the hydrolysis, at least one mineral acid, such as hydrochloric acid, sulfuric acid, phosphoric acid, or nitric acid is preferably used. After the acid treatment is performed, either by recrystallization using a recrystallizing solvent, such as ethyl acetate, toluene, hexane, or ether, or by distillation, a high-purity ω-hydroxy fatty acid can be obtained.

As the lactone used in the present invention, any compound represented by the following general formula (3) may be used:

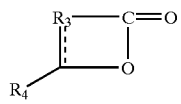

(3)

wherein $R_3$ is a carbon chain having 2 to 24 carbon atoms which is saturated or unsaturated by including at least one carbon-carbon double bond in any position, or a carbon chain having 8 to 24 carbon atoms, with at least one oxygen atom in any position, which is saturated or unsaturated by including at least one carbon-carbon double bond in any position, where an alkyl or alkylene group having 1 to 4 carbon atoms may be linked to any position as a side chain; $R_4$ is hydrogen, a hydroxyl group, or a carbon chain having 1 to 30 carbon atoms which is saturated or unsaturated by including at least one carbon-carbon double bond in any position, where an alkyl or alkylene group having 1 to 4 carbon atoms may be linked to any position; and the dashed line represents a single bond or a double bond. The industrial production methods for these compounds have been established, and the lactones used in the present invention may be produced by the known methods. However, these compounds have already been mass-produced as fragrance materials and high-purity products are easily obtainable. Most preferred examples of lactones include 12-dodecanolide, 15-pentadecanolide, 16-hexadecanolide, 11-pentadecen-15-olide, 12-pentadecen-15-olide, 7-hexadecen-16-olide, 9-hexadecen-16-olide, 10-oxahexadecanolide, 11-oxahexadecanolide, 12-oxahexadecanolide, 4-butanolide, 12-oxahexadecen-16-olide, 4-pentanolide, 4-hexanolide, 4-heptanolide, 4-octanolide, 4-nonanolide, 4-decanolide, 4-undecanolide, 4-dodecanolide, 4-tridecanolide, 4-tetradecanolide, 4-pentadecanolide, 4-hexadecanolide, 4-heptadecanolide, 4-octadecanolide, 4-nonadecanolide, 4-icosanolide, 4-methyl-4-decanolide, 5-hexanolide, 5-heptanolide, 5-octanolide, 5-nonanolide, 5-decanolide, 5-undecanolide, 5-dodecanolide, 5-tridecanolide, 5-tetradecanolide, 5-pentadecanolide, 5-hexadecanolide, 5-heptadecanolide, 5-octadecanolide, 5-icosanolide, 6-decanolide, 6-dodecanolide, 8-hexadecanolide, 10-hexadecanolide, 12-hexadecanolide, bovolide, dihydrobovolide, 2-decen-5-olide, 4-decen-5-olide, 5-decen-5-olide, 6-decen-6-olide, cis-7-decen-5-olide, 3-isopropyl-2-penten-5-olide, 3-methyl-2-buten-4-olide, and 2,3-dimethyl-2-penten-4-olide, and 3-hydroxy-4,5-dimethyl-2(5H)-furanone.

As the macrocyclic ketone used in the present invention, any compound represented by the following general formula (4) may be used:

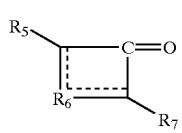

(4)

wherein $R_5$ is hydrogen or an alkyl or alkylene group having 1 to 4 carbon atoms, $R_6$ is a carbon chain having 7 to 17 carbon atoms which is saturated or unsaturated by including one or two carbon-carbon double bonds in any positions, where an alkyl or alkylene group having 1 to 4 carbon atoms may be linked to any position as a side chain, $R_7$ is hydrogen or an alkyl group or an alkylene group having 1 to 4 carbon atoms, and the dashed line represents a single bond or a double bond. The industrial production methods for the macrocyclic ketones have been established, and the macrocyclic ketones of the present invention may be produced by the known methods. However, these compounds have already been mass-produced as fragrance materials. For example, 5-cyclohexadecen-1-one, 8-cyclohexadecen-1-one, 3-methylcyclopentadecanone, and 9-cycloheptadecen-1-one, which are easily obtainable as high-purity products, are most preferable.

Furthermore, as the macrocyclic diester used in the present invention, any compound represented by the following general formula (5) may be used:

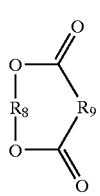

(5)

wherein $R_8$ is a carbon chain having 2 to 10 carbon atoms which is saturated or unsaturated by including at least one carbon-carbon double bond in any position, where an alkyl or alkylene group having 1 to 4 carbon atoms may be linked to any position; and $R_9$ is a carbon chain having 8 to 20 carbon atoms which is saturated or unsaturated by including at least one carbon-carbon double bond in any position. The industrial production methods for the macrocyclic diesters have been established, and the macrocyclic diesters used in the present invention may be produced by the known methods. However, these compounds have already been mass-produced as fragrance materials, and high-purity products are easily obtainable. Most preferred examples of macrocyclic diesters include ethylene dodecanedioate, ethylene tridecanedioate, ethylene tetradecanedioate, ethylene pentadecanedioate, ethylene hexadecanedioate, ethylene heptadecanedioate, ethylene octadecanedioate, ethylene nonadecanedioate, ethylene eicosanedioate, isopropylene dodecanedioate, isopropylene tridecanedioate, isopropylene tetradecanedioate, isopropylene pentadecanedioate, isopropylene hexadecanedioate, isopropylene heptadecanedioate, isopropylene octadecanedioate, isopropylene nonadecanedioate, isopropylene eicosanedioate, propylene dodecanedioate, propylene tridecanedioate, propylene tetradecanedioate, propylene pentadecanedioate, propylene hexadecanedioate, propylene heptadecanedioate, propylene octadecanedioate, propylene nonadecanedioate, propylene eicosanedioate, butylene dodecanedioate, butylene tridecanedioate, butylene tetradecanedioate, butylene pentadecanedioate, butylene hexadecanedioate, butylene heptadecanedioate, butylene octadecanedioate, butylene nonadecanedioate, and butylene eicosanedioate.

With respect to the compounds used as anticancer agents in the present invention, for example, if they have optical isomerism, racemic mixtures may be acceptable, and it is possible to select the ratio thereof arbitrarily up to an optical purity of 100%. For example, if the compounds have geometrical isomerism, it is possible to select the ratio thereof arbitrarily from 0 to 100%.

Examples of the bases constituting the salts of the ω-hydroxy fatty acids or hydroxy oxo-fatty acids used in the present invention include, but are not limited to, alkaline metals, such as sodium and potassium, and alkaline-earth metals, such as calcium and magnesium, and examples of the organic bases constituting the salts include, but are not limited to, trimethylamine, triethylamine, pyridine, ethanolamine, diethanolamine, and dicyclohexylamine.

Examples of the esters of the ω-hydroxy fatty acids or hydroxy oxo-fatty acids used in the present invention include, but are not limited to, esters with monools, such as methanol, ethanol, 1-propanol; esters with diols, such as ethylene glycol and propylene glycol; esters with triols, such as glycerol; and esters with sugars, such as glucose and sucrose, but are not limited thereto.

With respect to the ω-hydroxy fatty acids and salts or esters thereof, hydroxy oxo-fatty acids and salts or esters thereof, lactones, macrocyclic ketones, and macrocyclic diesters, since the cytotoxicity is significantly low compared to the traditional anticancer agents, it is possible to administer them to mammals including humans orally or parenterally, for example, by inhalation, percutaneous absorption, nasal absorption, rectal absorption, instillation, intravascular injection, and subcutaneous injection.

The anticancer agents of the present invention may be formulated in any dosage form, for example, as liquid drugs, orally administered drugs, tablets, powders, suppositories, external preparations, bath preparations, pastes, plasters, eye drops, intravenously injectable solutions, powdered drug, granules, sugar-coated tablets, capsules, pills, suspensions, ampoules, parenteral solutions, and inhalants, by mixing with various types of known carriers which are pharmacologically acceptable liquids or solids and by adding thereto, as necessary, stabilizers, colorants, corrigents, flavoring substances, diluting agents, solvents, surface active agents, emulsifiers, suspending agents, dispersants, preservatives, solubilizing agents, isotonizing agents, buffer agents, soothing agents, moisturizing agents, binders, coating materials, glazing agents, disintegrating agents, etc.

Additionally, among the compounds used in the present invention, for example, 15-pentadecanolide is known to have a superior property as a transdermal absorption promoting agent (e.g., as disclosed in Japanese Patent No. 2583777 and JP-A-4-275217). Therefore, when an external preparation for skin or plaster is formulated by mixing the 15-pentadecanolide with other active ingredients and clinically used, the 15-pentadecanolide by itself acts as an anticancer agent, and it is also expected that the rate of transdermal absorption of other active ingredients be increased. From this viewpoint, the present invention can also provide breakthrough anticancer agents which are not conventionally available.

The content of the anticancer agents of the present invention, i.e., at least one compound selected from the group consisting of ω-hydroxy fatty acids and salts or esters thereof, hydroxy oxo-fatty acids and salts or esters thereof, lactones, macrocyclic ketones, and macrocyclic diesters, is preferably 0.001 to 100% by weight in a preparation or composition.

With respect to at least one compound selected from the group consisting of ω-hydroxy fatty acids and salts or esters thereof, hydroxy oxo-fatty acids and salts or esters thereof, lactones, macrocyclic ketones, and macrocyclic diesters used in the present invention, although it depends on symptoms, age, gender, body weight, dosage form, or administration mode, the effective dose per day for an adult is usually 0.001 to 10,000 mg/kg, and preferably 1 to 100 mg/kg in the case of oral administration, suppositories, external preparations, and the like, and the effective dose per day for an adult is usually 0.01 to 200 mg/kg, and preferably 0.25 to 100 mg/kg in the case of intravenous injection and drip infusion, in a single or divided dose.

The anticancer agents of the present invention are effective in treating mammals in general having tumors, and are drugs which are remarkably effective in prolonging lives of the tumor bearing animals and in inhibiting metastasis of cancer.

Examples of diseases to which the anticancer agents of the present invention are targeted include various benign and malignant tumors, such as malignant melanoma, malignant lymphoma, pharyngeal cancer, laryngeal cancer, gastric cancer, Kaposi's sarcoma, liver cancer, myosarcoma, colonic cancer, angioma, myeloma, thyroid cancer, testicular tumor, pancreatic cancer, cancer of the digestive organs, esophageal cancer, large bowel cancer, cancer of the upper jaw, lingual cancer, labial cancer, oral cancer, gallbladder cancer, bile duct cancer, biliary tract cancer, rectal cancer, mammary cancer, ureteral tumor, sarcoma, osteogenic sarcoma, brain tumor, leukemia, lung cancer, neuroblastoma, polycythemia vera, bladder tumor, ovarian cancer, uterine cancer, prostate cancer, myosarcoma, skin cancer, basal cell cancer, skin appendage cancer, metastatic skin cancer, and skin melanoma.

It is possible to enhance the anticancer effect by combining at least one compound selected from the group consisting of ω-hydroxy fatty acids and salts or esters thereof, hydroxy oxo-fatty acids and salts or esters thereof, lactones, macrocyclic ketones, and macrocyclic diesters as the active ingredient in the anticancer agents of the present invention with a specific known antitumor agent. Examples of antitumor agents which show such a synergistic effect include at least one agent selected from the group consisting of angiostatic steroid coexistent with heparin, aceglatone, actinomycin D, adriamycin, ifosfamide, Estracyt (registered trade name), etoposide, enocitabine, epitiostanol, aclarubicin hydrochloride, ancitabine hydrochloride, daunorubicin hydrochloride, doxorubicin hydrochloride, nimustine hydrochloride, procarbazine hydrochloride, carboquone, carboplatin, carmofur, tamoxifen citrate, Krestin (registered trade name), chromomycin A3, antitumor polysaccharides, antitumor platelet factors, cyclophosphamide, cisplatin, Schizophyllan, cytarabine, dacarbazine, thioinosine, thiotepa, tegafur, Nitromin (registered trade name), neocarzinostatin, OK-432, vincristine, vindesine, bleomycin, fluorouracil, furtulon, broxuridine, Protecton (registered trade name), busulfan, pepleomycin, honvan, Mitomycin C (registered trade name), methotrexate, peplomycin, VePesid (registered trade name), Bestatin (registered trade name), interferon-β, mepitiostane, mitobronitol, mercaptopurine, merphalan, laminin peptides, vincristine sulfate, vindesine sulfate, vinblastine sulfate, bleomycin sulfate, peplomycin sulfate, lentinan, MDS Kowa 3000 (registered trade name), UFT (registered trade name), and various types of interferons.

When another antitumor agents and at least one compound selected from the group consisting of ω-hydroxy fatty acids and salts or esters thereof, hydroxy oxo-fatty acids and salts or esters thereof, lactones, macrocyclic ketones, and macrocyclic diesters used in the present invention are combined, the dosage of the compound of the present invention is selected from the range for the independent dosage described above, and the dosage of the other antitumor agents to be combined is also selected from the range for the independent dosage (concentration) clinically administered. The dosage may be adjusted appropriately.

When the existing antitumor agents are administered to an organism and in the case of a human body, various side effects may be generated, for example, leukopenia, thrombocytopenia, loss of appetite, vomiting, stomatitis, diarrhea, exanthema, alopecia, chromatosis, fever, headache, liver function failure, proteinuria, and edema. However, if the existing antitumor agents are combined with at least one compound selected from the group consisting of ω-hydroxy fatty acids and salts or esters thereof, hydroxy oxo-fatty acids and salts or esters thereof, lactones, macrocyclic ketones, and macrocyclic diesters, which are the active ingredients of the present invention, since a small dose of the compound used in the present invention has the anticancer effect, the content of the existing antitumor agents can be decreased, resulting in a reduction in the side effects of the existing antitumor agents.

In another aspect, the anticancer agents of the present invention can be added to a toiletry article. Examples of the toiletry articles to which the anticancer agents of the present invention can be added are perfume, eau de cologne, lotion, milky lotion, cream, gel, nourishing lotion, pack agents, after-shave lotion, foundation, face powder, lip sticks, rouge, nail treatments, shampoos, rinses, hair growth agents, hair-dyeing agents, soaps, cleansing lotion, sun care products, deodorants, toothpaste, and mouthwash.

The content of the anticancer agents of the present invention is preferably 0.001 to 10.0% by mass of the toiletry article.

It is also possible to add the anticancer agents of the present invention to the toiletry articles described above in combination with other medicinal properties.

In another aspect, the anticancer agents of the present invention can be added to a food. Examples of the foods to which the anticancer agents of the present invention can be added include drinks, such as soft drinks, fruit drinks, alcoholic beverages, milk beverages, and luxury drinks; confectionery, such as chocolates, cookies, chewing gum, candies, snacks, and jelly; cereals; seasoning; spices; edible oil; cooked food; processed agricultural products; processed meat products; processed marine products; hospital diet; and fluid diet. The content of the anticancer agents of the present invention is preferably 0.001 to 10.0% by mass of the food.

It is also possible to add the anticancer agents of the present invention to the foods described above in combination with other medicinal properties.

By adding the anticancer agents of the present invention to the toiletry articles and the foods, the effect of preventing cancer and the effect of preventing the recurrence of cancer, in particular, can be expected.

EXAMPLE

The present invention will be described below based on the examples of production methods, preparations, and effect tests. However, it is to be understood that the present invention is not limited thereto.

Syntheses Example 1

Synthesis of 15-hydroxy-11(12)-pentadecenoic Acid

In a reflux apparatus, 10.0 g (0.042 mol) of 11(12)-pentadecen-15-olide and 42 g (0.053 mol) of 5% sodium hydroxide aqueous solution were prepared and reflux was performed for 3 hours. After unreacted materials were removed from the refluxed solution using 50 g of toluene, acidification was performed with diluted sulfuric acid and 15-hydroxy-11 (12)-pentadecenoic acid was extracted using ethyl acetate. The extract was washed with a saturated saline solution until the neutral point was reached, and the solvent was recovered to obtain 10.83 g of crystals. The crystals were dissolved in 75g of toluene, and recrystallization was performed by cooling to 5° C. The mother liquor was removed by filtration, followed by rinsing with toluene which was cooled to 5° C. The resultant crystals were dried under reduced pressure, and thereby 9.68 g of 15-hydroxy-11 (12)-pentadecenoic acid was obtained. The product was methyl esterified. As a result of gas chromatography, the purity was 98% as a mixture of isomers, and the yield was 88 mol %.

Synthesis Example 2

Synthesis of 16-hydroxy-13-oxohexadecanoic Acid

In a reflux apparatus, 62.17 g (0.254 mol) of brassylic acid, 65.2 g (2.03 mol) of methanol, and 1.0 g of concentrated sulfuric acid were prepared and reflux was performed for 3 hours. The refluxed solution was neutralized by adding 1.1 g of sodium carbonate, and then excess methanol was recovered. Distillation was then performed under reduced pressure to obtain 61.12 g of brassylic acid dimethyl ester, to which 4.83 g (0.056 mol) of γ-butyrolactone and 10.82 g (0.056 mol) of 28% methanol solution of sodium methylate were added, followed by heating to 105° C. under normal pressure. Furthermore, the pressure was reduced to 680 hPa, and methanol was recovered. After the pressure was reset to normal and the temperature was decreased to 50° C., 100 g of n-hexane was added thereto. Next, 74.8g of 3% sodium hydroxide aqueous solution were added thereto, and an aqueous layer was obtained by separation. After heating at 90° C. for 2 hours, oil-soluble by-products were removed using toluene. The sodium salt of the target substance was precipitated by cooling to 20° C., and crystals were separated by filtration. Rinsing was performed with water at 5° C., and the resultant crystals were acidified with diluted sulfuric acid. Extraction was performed with ethyl acetate, and the extract was washed with a saturated saline solution until the neutral point was reached. By cooling to 5° C., crystals were precipitated and separated by filtration. The crystals were dried under reduced pressure, and thereby 10.84 g of the target 16-hydroxy-13-oxohexadecanoic acid were obtained. As a result of gas chromatography, the purity was 99%, and the yield was 15 mol %.

| (Preparation Example 1) Tablet | |
|---|---|
| 15-hydroxypentadecanoic acid | 10 g |
| 6% HPC milk sugar | 80 g |
| Magnesium stearate | 4 g |
| Potatostarch | 6 g |

The above ingredients were mixed well, and formed into tablets with a tablet machine, and 250 mg tablets containing 25 mg of 15-hydroxypentadecanoic acid were obtained.

Preparation Example 2

Injection

Into a physiological saline solution for injection, 1 g of sterilized 15-hydroxy-12-oxopentadecanoic acid was dissolved so that the total amount was 100 ml, followed by filtration with a 0.2 μm membrane filter. A 10 ml-volume of the resultant solution was filled into an ampoule for injection.

Preparation Example 3

Capsule

A mixture of 200 mg of 9-hexadecen-16-olide, 750 mg of cornstarch, and 50 mg of magnesium stearate was filled into a gelatine capsule, and a capsule was thereby obtained.

Preparation Example 4

Paste

The ingredients described below were prepared in the usual manner and a paste was obtained.

| White petrolatum | 20.0 (% by weight) |
|---|---|
| Stearyl alcohol | 22.0 (% by weight) |
| Propylene glycol | 12.0 (% by weight) |
| Sodium lauryl sulfate | 1.5 (% by weight) |
| Paraben | 0.2 (% by weight) |
| 15-pentadecanolide | 3.0 (% by weight) |

| -continued | |
|---|---|
| 5-cyclohexadecen-1-one | 2.0 (% by weight) |
| Purified water | 39.3 (% by weight) |

Effect Test Example 1

Cancer Cell Mobility Test (Cancer Invasion Inhibitory Action Test) (In Vitro)

A Boyden double chamber was used, in which a porous film with 8 μm pores was placed, the upper surface of the porous film being coated with Matrigel as a reconstructed membrane, the lower surface of the porous film being coated with fibronectin as an extracellular matrix. In the upper compartment of the chamber, 200,000 cells of melanoma cell line B16BL6, a type of skin cancer, were inoculated, and after 3.5 hours, Diff Quick staining was performed and the number of invasive cancer cells invading the lower compartment was counted using a CCD camera/multibioscanner. The cancer invasion inhibitory action of the compounds of the present invention was confirmed, as shown in Table 1 below. The compounds of the present invention were administered to cancer cells for 18 hours in advance at amounts of 5 μM and 20 μM. The results thereof are shown in Table 1. With respect to the compounds that were remarkably effective among the compounds of the present invention, for example, 15-hydroxypentadecanoic acid, 15-hydroxy-12-oxopentadecanoic acid, 9-hexadecen-16-olide, and 5-cyclohexadecen-1-one, the cancer invasion was inhibited to approximately 20 to 30% by the administration of a significantly low concentration of 20 μM. When the results of the examples of the present invention were compared to derivatives of L-ascorbic acid, which are known as remarkably effective cancer metastasis inhibitors (disclosed in Jp-A-8-291075, etc.), a 25% cancer cell invasion inhibition was obtained at a concentration of approximately 280 μM with respect to L-ascorbyl 2-phosphate, and a 25% cancer cell invasion inhibition was obtained at a concentration of approximately 110 μM with respect to L-ascorbyl 6-O-palmitate, while it was found that the compounds of the present invention had a strong cancer invasion inhibitory action which was 5 to 14 times that of the conventional compounds.

TABLE 1

| | Tumor Invasion (cell/mm$^2$) | | Cell Invasion Rate at 20 μM |
|---|---|---|---|
| Compound Name | 5 μM | 20 μM | (%) |
| (Hydroxy acids) | | | |
| No addition | 503 ± 42 | — | — |
| 12-hydroxydodecanoic acid | 324 ± 23 | 246 ± 30 | 48.9 |
| 15-hydroxypentadecanoic acid | 289 ± 45 | 135 ± 11 | 26.8 |
| 16-hydroxyhexadecanoic acid | 301 ± 47 | 199 ± 32 | 39.6 |
| (Hydroxy oxo-acids) | | | |
| 15-hydroxy-12-oxopentadecanoic acid | 268 ± 34 | 119 ± 25 | 23.7 |

TABLE 1-continued

| Compound Name | Tumor Invasion (cell/mm²) 5 μM | Tumor Invasion (cell/mm²) 20 μM | Cell Invasion Rate at 20 μM (%) |
|---|---|---|---|
| (Lactones) | | | |
| 12-dodecanolide | 405 ± 38 | 461 ± 67 | 91.7 |
| 15-pentadecanolide | 386 ± 26 | 324 ± 27 | 64.4 |
| 11(12)-pentadecen-15-olide | 234 ± 17 | 146 ± 31 | 29.0 |
| 16-hexadecanolide | 370 ± 62 | 293 ± 43 | 58.3 |
| 9-hexadecen-16-olide | 257 ± 42 | 113 ± 19 | 22.5 |
| (Macrocyclic ketones) | | | |
| No addition | 452 ± 33 | | — |
| Cyclopentadecanone | 459 ± 39 | 491 ± 35 | 108.6 |
| 5-cyclohexadecen-1-one | 285 ± 36 | 143 ± 14 | 31.6 |

* In Table 1, the cell invasion rate is calculated relative to the case of no addition, which is assumed to be 100%, and the lower value indicates the higher degree of invasion inhibitory action.

Effect Test Example 2

Cancer Cell Mobility Test (Cancer Invasion Inhibitory Action Test) (In Vitro)

A Boyden double chamber was used, in which a porous film with 8 μm pores was placed, the upper surface of the porous film being coated with Matrigel as a reconstructed membrane, the lower surface of the porous film being coated with fibronectin as an extracellular matrix. In the upper compartment of the chamber, 200,000 cells of human fibrosarcoma cell line HT1080 were inoculated, and after 3.5 hours, Diff Quick staining was performed and the number of invasive cancer cells invading the lower compartment was counted using a CCD camera/multibioscanner. The cancer invasion inhibitory action of the compounds of the present invention was confirmed as shown in Table 2 below. The compounds of the present invention were administered to cancer cells for 18 hours in advance at amounts of 5 μM and 10 μM. The results thereof are shown in Table 2. With respect to the compounds that were remarkably effective among the compounds of the present invention, for example, 16-hydroxy-13-oxohexadecanoic acid, ethylene tridecanedioate, 5-hexadecanolide, 12-oxahexadecen-16-olide, and ethyl-16-hydroxy-9-hexadecenoate, the cancer invasion was inhibited to approximately 16 to 30% even by the administration of a significantly low concentration of 10 μM. These compounds of the present invention showed superior results compared to Marimastat (trade name/manufactured by British Biotech), which is known as a remarkably effective cancer metastasis inhibitor.

TABLE 2

| Compound Name | Tumor Invasion (cell/mm²) 5 μM | Tumor Invasion (cell/mm²) 10 μM | Cell Invasion Rate at 10 μM (%) |
|---|---|---|---|
| (Hydroxy oxo-acids) | | | |
| No addition | 380 | | — |
| 16-hydroxy-13-oxohexadecanoic acid | 214 | 121 | 31.8 |
| (Esters) | | | |
| No addition | 370 | | — |
| ethyl-15-hydroxy-11(12)-pentadecenoate | 129 | 106 | 28.6 |
| (Macrocyclic ether lactones) | | | |
| No addition | 524 | | — |
| 12-oxahexadecen-16-olide | 218 | 109 | 20.8 |
| (Lactones) | | | |
| No addition | 404 | | — |
| 5-hexadecanolide | 144 | 111 | 27.5 |
| (Macrocyclic diesters) | | | |
| No addition | 524 | | — |
| Ethylene tridecanedioate | 226 | 84 | 16.0 |
| No addition | 404 | | — |
| Marimastat (cancer metastasis inhibitor) | 269 | 172 | 42.6 |

* In Table 2, the cell invasion rate is calculated relative to the case of no addition, which is assumed to be 100%, and the lower value indicates the higher degree of invasion inhibitory action.

Effect Test Example 3

Cancer Metastasis Inhibitory Action Test (In Vivo)

Rat spontaneous mammary cancer cells (SST-2) ($1\times10^5$ cells) were subcutaneously implanted in the backs of Wister male rats (5 rats for each group). After 35 days, the rats were sacrificed, and the lung weight and the number of colonies formed were measured to observe the extent of lung metastasis of the SST-2. With respect to the groups to which 5-cyclohexadecen-1-one as the compound of the present invention was administered, 20 mg/rat and 5 mg/rat were orally administered and subcutaneously injected, from day 7 pre-implant to day 34 post-implant, and the subcutaneous tumor weight, the lung weight, and the number of metastatic colonies formed were compared with those of the control group, to which no treatment was provided. The results thereof are shown in Table 3. As is obvious from the table, a significantly definite lung metastasis inhibiting action was confirmed with respect to the areas to which 5-cyclohexadecen-1-one was administered.

TABLE 3

| 5-cyclohexadecen-1-one dosage (mg/rat) | Subcutaneous tumor weight (g) | Lung weight (g) | Average number of metastatic colonies formed |
|---|---|---|---|
| No addition | 41.8 | 4.9 | 96.9 |
| Oral Administration 5 | 46.4 | 1.5 | 28.4 |
| Oral Administration 20 | 44.7 | 1.4 | 17.5 |
| Subcutaneous injection 5 | 43.5 | 1.3 | 15.7 |

TABLE 3-continued

| 5-cyclohexadecen-1-one dosage (mg/rat) | Subcutaneous tumor weight (g) | Lung weight (g) | Average number of metastatic colonies formed |
|---|---|---|---|
| Subcutaneous injection 20 | 42.0 | 1.1 | 10.9 |

Effect Test Example 4

Cancer Metastasis Inhibitory Action Test (In Vivo)

Rat spontaneous mammary cancer cells (SST-2) ($1 \times 10^5$ cells) were subcutaneously implanted in the back of male Wister rats (5 rats for each group). After 35 days, the rats were sacrificed, and the lung weight and the number of colonies formed were measured to observe the extent of lung metastasis of the SST-2. Testing was conducted for the group to which 15-hydroxypentadecanoic acid, as the compound of the present invention, was administered alone and for the groups to which this compound was administered in combination with the known anticancer agents described below. With respect to the compound of the present invention, 50 mg/day/rat was orally administered from day 7 pre-implant to day 34 post-implant, and with respect to the known anticancer agents, the minimum dose for each anticancer agent according to the literature (Pharmaceutical Directory; Jiho, Inc., 1989, Fourth Edition, 1474–1509) was orally administered, and the subcutaneous tumor weight, the lung weight, and the number of colonies formed were compared with those of the group to which the compound of the present invention was administered. As a result, the known anticancer agents described below showed higher effects of inhibiting cancer metastasis when combined, compared to the dosage of the 15-hydroxypentadecanoic acid of the present invention alone. Consequently, the higher inhibitory action of cancer metastasis to the lung was confirmed with respect to the 15-hydroxypentadecanoic acid of the present invention in combination with the known anticancer agents listed below.

Actinomycin D, aceglatone, ifosfamide, enocitabine, aclarubicin hydrochloride, ancitabine hydrochloride, nimustine hydrochloride, daunorubicin hydrochloride, doxorubicin hydrochloride, procarbazine hydrochloride, Estracyt (registered trade name), carboquone, carmofur, chromomycin A3, Krestin (registered trade name), tamoxifen, cyclophosphamide, cisplatin, Schizophyllan, cytarabine, dacarbazine, thioinosine, thiotepategafur, Nitromin (registered trade name), neocarzinostatin, pitiostanol, OK-432, fluorouracil, busulfan, Protecton (registered trade name), broxuridine, angiostatic steroid containing heparin, honvan, Mitomycin C (registered trade name), mitobronitol, methotrexate, mepitiostane, mercaptopurine, merphalan, vinblastine, vincristine sulfate, vindesine sulfate, peplomycin, VePesid (registered trade name), Bestatin (registered trade name), interferon-β, bleomycin, peplomycin sulfate, lentinan, L-asparaginase, MDS Kowa 3000 (registered trade name), UFT (registered trade name), CDPGYIGSR-NH$_2$ Effect Test Example 5

Cancer Metastasis Inhibitory Action Test (In Vivo)

Cancer cells of B-16 melanoma cell line BL were incubated in a 5% CO$_2$ incubator using an MEM culture medium (containing 10% FBS), and the individual cells were dissociated with a 2.5% trypsin solution. The melanoma cells were injected into the caudal vein of BDF1 mice (SPF). The number of cells injected was $2 \times 10^5/0.2$ ml/mouse. As test compounds for cancer metastasis inhibitory action, 15-hydroxypentadecanoic acid, 15-pentadecanolide, and 5-cyclohexadecen-1-one were used, and as a positive control compound, Mitomycin Kyowa S (manufactured by Kyowa Hakko Kokyo Co., Ltd.) was used. The test compounds and the positive control compound were dissolved or suspended in olive oil and administered as shown in Table 5 below. (In the case of intravenous administration, micellisation was performed using Tween before administration.) The dosage of the test compounds was 100 mg/kg each time in the case of peritoneal administration, and 10 mg/kg each time in the case of intravenous administration. The dosage of Mitomycin Kyowa S as the positive control compound was 0.5 mg/kg each time by peritoneal administration.

From day 10 post-implant onward, metastatic cancer cells of mice in the satellite group were observed, and on day 14 when the size of the cells was believed to be suitable for evaluation, the mice were sacrificed and the lungs were enucleated. The number of metastatic cancer cells was then counted.

TABLE 4

| Administration mode | Name of compound administered | Timing/Frequency (common to all compounds administered) |
|---|---|---|
| Peritoneal administration | 15-pentadecanolide | 1 day prior to implantation of cancer cells/Once |
|  | 5-cyclohexadecen-1-one | On the day of implantation of cancer cells/3 times (Immediately, 2 hours, and 4 hours after implantation) |
|  | 15-hydroxypentadecanoic acid | Day 1 and Day 2 post-implantation of cancer cells/3 times each (Morning, noon, and evening) |
| Peritoneal administration | Mitomycin (Positive control) | On the day of implantation of cancer cells/3 times (Immediately, 3 hours, and 6 hours after implantation) |
| Intravenous administration | 15-pentadecanolide | On the day of implantation of cancer cells/3 times (Immediately, 1 hour, and 2 hours after implantation) |

As a result, as shown in Table 5 below, the number of metastatic cells was smaller for every test compound compared to the case of no administration, and the cancer metastasis inhibitory action was confirmed. Additionally, with respect to the administration of the test compounds, a significant decrease in the weight of mice was not observed in any compound even for 14 days until sacrifice.

TABLE 5

| Name of compound administered | Number of metastatic cells |
|---|---|
| No administration (Peritoneal administration) | 139.8 |
| 15-pentadecanolide | 134.3 |
| 5-cyclohexadecen-1-one | 35.6 |

TABLE 5-continued

| Name of compound administered | Number of metastatic cells |
|---|---|
| 15-hydroxypentadecanoic acid | 78.0 |
| Mitomycin (positive control) (Intravenous administration) | 21.2 |
| 15-pentadecanolide | 52.2 |

* In Table 5, the number of metastatic cells is the mean value of 6 mice.

Effect Test Example 6

Test for Action of Killing Cancer (In Vivo)

In the backs of 6-week-old mice (first filial hybrid of C57BL/6 and DBA/2), $10^6$ cells of adenocarcinoma 755 cell line were subcutaneously implanted. After 24 hours, a solution in which each sample was suspended, at a concentration of 50 mg/ml, in a physiological saline solution of 0.25% surfactant Nikkol HCO-60 (manufactured by Nikko Chemicals Co., Ltd.; polyoxyethylene (40) hydrogenated castor oil), was subcutaneously injected into a group of 8 mice, daily at 10 mg/kg for 5 days. On day 10 post-implant of adenocarcinoma 755 cells, the mice were sacrificed and tumors were excised. The average weight (g) of the tumors was obtained. As a result, the average weight of the control group was 9.0 g, while the average weight of the group to which 5-cyclohexadecen-1-one had been administered was as small as 1.9 g. The significant action of killing cancer was thus confirmed.

Industrial Applicability

With respect to a drug containing, as an active ingredient, at least one compound selected from the group consisting of ω-hydroxy fatty acids and salts or esters thereof, hydroxy oxo-fatty acids and salts or esters thereof, lactones, macrocyclic ketones, and macrocyclic diesters, since the activities of killing cancer and inhibiting cancer metastasis are significantly high, the cytotoxicity is significantly low, and a small dose is effective, it is possible to provide an anticancer agent having significantly decreased side effects. Additionally, use in combination with known antitumor agents can further enhance the activity of inhibiting cancer metastasis. Among the anticancer agents of the present invention, ω-hydroxy fatty acids can be easily obtained in high purities by hydrolyzing lactones which are also the anticancer agents of the present invention.

What is claimed is:

1. An anticancer agent comprising, as an active ingredient, at least one compound selected from the group consisting of:

an ω-hydroxy fatty acid represented by general formula (1) or a salt or ester thereof:

$$HO-R_1-COOH \quad (1)$$

wherein $R_1$ is a straight carbon chain having 10 to 25 carbon atoms, with no or one double bond, where an alkyl or alkylene group having 1 to 4 carbon atoms or a hydroxyl group may be linked to any position as a side chain;

a hydroxy oxo-fatty acid represented by general formula (2) or a salt or ester thereof:

$$R_2-COOH \quad (2)$$

wherein $R_2$ is a saturated straight carbon chain having 9 to 25 carbon atoms, with at least one carbonyl group and at least one hydroxyl group, where an alkyl or alkylene group having 1 to 4 carbon atoms may be linked to any position as a side chain;

a lactone represented by general formula (3):

wherein $R_3$ is a carbon chain having 2 to 24 carbon atoms which is saturated or unsaturated by including at least one carbon-carbon double bond in any position, or a carbon chain having 8 to 24 carbon atoms with at least one oxygen atom in any position which is saturated or unsaturated by including at least one carbon-carbon double bond in any position, where an alkyl or alkylene group having 1 to 4 carbon atoms may be linked to any position as a side chain; $R_4$ is hydrogen, a hydroxyl group, or a carbon chain having 1 to 30 carbon atoms which is saturated or unsaturated by including at least one carbon-carbon double bond in any position, where an alkyl or alkylene group having 1 to 4 carbon atoms may be linked to any position; and the dashed line represents a single bond or a double bond;

a macrocyclic ketone represented by general formula (4):

wherein $R_5$ is hydrogen or an alkyl or alkylene group having 1 to 4 carbon atoms; $R_6$ is a carbon chain having 7 to 17 carbon atoms which is saturated or unsaturated by including at least one carbon-carbon double bond in any position, where an alkyl or alkylene group having 1 to 4 carbon atoms may be linked to any position as a side chain; $R_7$ is hydrogen or an alkyl or alkylene group having 1 to 4 carbon atoms; and the dashed line represents a single bond or a double bond; and a macrocyclic diester represented by general formula (5)

wherein $R_8$ is a carbon chain having 2 to 10 carbon atoms which is saturated or unsaturated by including at least one carbon-carbon double bond in any position, where an alkyl or alkylene group having 1 to 4 carbon atoms may be linked to any position; and $R_9$ is a carbon chain having 8 to 20 carbon atoms which is saturated or unsaturated by including at least one carbon-carbon double bond in any position.

2. An anticancer agent according to claim 1, wherein the salt of the ω-hydroxy fatty acid and/or the hydroxy oxo-fatty acid is any one of a sodium salt, a potassium salt, a magnesium salt, a calcium salt, and an aluminum salt.

3. An anticancer agent according to claim 1, wherein the ester of the w-hydroxy fatty acid and/or the hydroxy oxo-fatty acid is any one of a methyl ester, an ethyl ester, an n-propyl ester, an isopropyl ester, an n-butyl ester, a sec-butyl ester, and a tert-butyl ester.

4. An anticancer agent according to claim 1, wherein the hydroxy oxo-fatty acid, or the salt or ester thereof has a hydroxyl group in the w position.

5. An anticancer agent according to claim 1, wherein the hydroxy oxo-fatty acid, or the salt or ester thereof has a carbonyl group in the w-3 position.

6. An anticancer agent according to claim 1, wherein the compound represented by any one of the general formulae (1) to (5) is at least one of 14-hydroxytetradecanoic acid, 15-hydroxypentadecanoic acid, 16-hydroxyhexadecanoic acid, 17-hydroxyheptadecanoic acid, 18-hydroxyoctadecanoic acid, 15-hydroxy-11-pentadecenoic acid, 15-hydroxy-12-pentadecenoic acid, 16-hydroxy-9-hexadecenoic acid, 16-hydroxy-7-hexadecenoic acid, 11-hydroxy-8-oxoundecanoic acid, 12-hydroxy-9-oxoundecanoic acid, 13-hydroxy-10-oxotridecanoic acid, 14-hydroxy-11-oxotetradecanoic acid, 15-hydroxy-12-oxopentadecanoic acid, 16-hydroxy-13-oxohexadecanoic acid, 17-hydroxy-14-oxoheptadecanoic acid, 18-hydroxy-15-oxooctadecanoic acid, 19-hydroxy-16-oxononadecanoic acid, 20-hydroxy-17-oxoeicosanoic acid, 21-hydroxy-18-oxoheneicosanoic acid, 12-dodecanolide, 15-pentadecanolide, 16-hexadecanolide, 11-pentadecen-15-olide, 12-pentadecen-15-olide, 7-hexadecen-16-olide, 9-hexadecen-16-olide, 5-cyclohexadecen-1-one, 8-cyclohexadecen-1-one, 3-methylcyclopentadecanone, 9-cycloheptadecen-1-one, 10-oxahexadecanolide, 11-oxahexadecanolide, 12-oxahexadecanolide, 4-butanolide, 12-oxahexadecen-16-olide, 4-pentanolide, 4-hexanolide, 4-heptanolide, 4-octanolide, 4-nonanolide, 4-decanolide, 4-undecanolide, 4-dodecanolide, 4-tridecanolide, 4-tetradecanolide, 4-pentadecanolide, 4-hexadecanolide, 4-heptadecanolide, 4-octadecanolide, 4-nonadecanolide, 4-icosanolide, 4-methyl-4-decanolide, 5-hexanolide, 5-heptanolide, 5-octanolide, 5-nonanolide, 5-decanolide, 5-undecanolide, 5-dodecanolide, 5-tridecanolide, 5-tetradecanolide, 5-pentadecanolide, 5-hexadecanolide, 5-heptadecanolide, 5-octadecanolide, 5-icosanolide, 6-decanolide, 6-dodecanolide, 8-hexadecanolide, 10-hexadecanolide, 12-hexadecanolide, bovolide, dihydrobovolide, 2-decen-5-olide, 4-decen-5-olide, 5-decen-5-olide, 6-decen-6-olide, cis-7-decen-5-olide, 3-isopropyl-2-penten-5-olide, 3-methyl-2-buten-4-olide, 2,3-dimethyl-2-penten-4-olide, ethylene dodecanedioate, ethylene tridecanedioate, ethylene tetradecanedioate, ethylene pentadecanedioate, ethylene hexadecanedioate, ethylene heptadecanedioate, ethylene octadecanedioate, ethylene nonadecanedioate, ethylene eicosanedioate, isopropylene dodecanedioate, isopropylene tridecanedioate, isopropylene tetradecanedioate, isopropylene pentadecanedioate, isopropylene hexadecanedioate, isopropylene heptadecanedioate, isopropylene octadecanedioate, isopropylene nonadecanedioate, isopropylene eicosanedioate, propylene dodecanedioate, propylene tridecanedioate, propylene tetradecanedioate, propylene pentadecanedioate, propylene hexadecanedioate, propylene heptadecanedioate, propylene octadecanedioate, propylene nonadecanedioate, propylene eicosanedioate, butylene dodecanedioate, butylene tridecanedioate, butylene tetradecanedioate, butylene pentadecanedioate, butylene hexadecanedioate, butylene heptadecanedioate, butylene octadecanedioate, butylene nonadecanedioate, and butylene eicosanedioate.

7. An anticancer agent comprising:

at least one of the w-hydroxy fatty acid, or the salt or ester thereof, the hydroxy oxo-fatty acid, or the salt or ester thereof, the lactone, the macrocyclic ketone, and the macrocyclic diester according to claim 1; and another antitumor agent used in combination therewith.

8. An anticancer agent according to claim 1, wherein the w-hydroxy fatty acid, or the salt or ester thereof is obtained by hydrolyzing a lactone.

9. An anticancer agent according to claim 1, wherein the hydroxy fatty acid, or the salt or ester thereof is obtained by hydrolyzing a lactone, followed by recrystallization, or purification by distillation.

10. A drug containing, as an active ingredient, at least one of the compounds represented by the general formulae (1) to (5) according to claim 1.

11. A toiletry article containing at least one of the compounds represented by the general formulae (1) to (5) according to claim 1.

12. A food containing at least one of the compounds represented by the general formulae (1) to (5) according to claim 1.

13. An anticancer agent comprising, as an active ingredient, at least one compound selected from the group consisting of:

an ω-hydroxy fatty acid represented by general formula (1) or a salt thereof:

HO—R$_1$—COOH  (1)

wherein R$_1$ is a straight carbon chain having 10 to 25 carbon atoms, with no or one double bond, where an alkyl or alkylene group having 1 to 4 carbon atoms or a hydroxyl group may be linked to any position;

a hydroxy oxo-fatty acid represented by general formula (2) or a salt thereof:

R$_2$—COOH  (2)

wherein R$_2$ is a saturated straight carbon chain having 9 to 25 carbon atoms, with at least one carbonyl group and at least one hydroxyl group, where an alkyl or alkylene group having 1 to 4 carbon atoms may be linked to any position as a side chain;

a macrocyclic lactone represented by general formula (3):

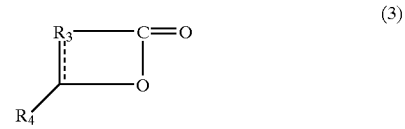

wherein R$_3$ is a carbon chain having 8 to 24 carbon atoms which is saturated or unsaturated by including one or two carbon-carbon double bonds in any positions, where an alkyl or alkylene group having 1 to 4 carbon atoms may be linked to any position; R$_4$ is hydrogen or an alkyl or alkylene group having 1 to 4 carbon atoms; and the dashed line represents a single bond or a double bond; and a macrocyclic ketone represented by general formula (4):

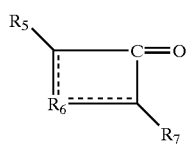
(4)

wherein $R_5$ is hydrogen or an alkyl or alkylene group having 1 to 4 carbon atoms; $R_6$ is a carbon chain having 7 to 17 carbon atoms which is saturated or unsaturated by including one or two carbon-carbon double bonds in any position, where an alkyl or alkylene group having 1 to 4 carbon atoms may be linked to any position; $R_7$ is hydrogen or an alkyl or alkylene group having 1 to 4 carbon atoms; and the dashed line represents a single bond or a double bond.

14. An anticancer agent according to claim 1, wherein the compound represented by the general formula (1) is 15-hydroxy-11-pentadecenoic acid or 15-hydroxy-12-pentadecenoic acid.

15. An anticancer agent according to claim 1, wherein the compound represented by the general formula (2) is 16-hydroxy-13-oxohexadecanoic acid.

16. An anticancer agent according to claim 1, wherein the compound represented by the general formula (3) is 12-oxahexadecen-16-olide.

17. An anticancer agent according to claim 1, wherein the compound represented by the general formula (4) is 5-hexadecanolide.

18. An anticancer agent according to claim 1, wherein the compound represented by the general formula (5) is ethylene tridecanedioate.

19. An anticancer agent according to claim 13, wherein the compound represented by the general formula (1) is 15-hydroxy-11-pentadecenoic acid or 15-hydroxy-12-pentadecenoic acid.

20. An anticancer agent according to claim 13, wherein the compound represented by the general formula (2) is 16-hydroxy-13-oxohexadecanoic acid.

21. An anticancer agent according to claim 13, wherein the compound represented by the general formula (3) is 12-oxahexadecen-16-olide.

22. An anticancer agent according to claim 13, wherein the compound represented by the general formula (4) is 5-hexadecanolide.

23. An anticancer agent according to claim 13, wherein the compound represented by the general formula (5) is ethylene tridecanedioate.

* * * * *

UNITED STATES PATENT AND TRADEMARK OFFICE
CERTIFICATE OF CORRECTION

PATENT NO.      : 6,639,089 B2
DATED           : October 28, 2003
INVENTOR(S)     : Ito et al.

It is certified that error appears in the above-identified patent and that said Letters Patent is hereby corrected as shown below:

Title page,
Item [22], please change "Nov. 1, 2001" to -- Nov. 5, 2001 --; and
Item [30], please change "Nov. 5, 2001" to -- Nov. 8, 2000 --.

Signed and Sealed this

Twentieth Day of April, 2004

JON W. DUDAS
*Acting Director of the United States Patent and Trademark Office*